US012611381B2

(12) United States Patent
Gan et al.

(10) Patent No.: US 12,611,381 B2
(45) Date of Patent: Apr. 28, 2026

(54) CATIONIC HYALURONIC ACID COATED SPANLASTICS AND PREPARATION AND APPLICATION THEREOF

(71) Applicants: FBC (Shanghai) Pharmaceutical Technology Co., Ltd., Shanghai (CN); Kewpie Corporation, Tokyo (JP)

(72) Inventors: Li Gan, Shanghai (CN); Yang Liu, Shanghai (CN); Hua Zhang, Shanghai (CN); Yanan Wang, Shanghai (CN); Jinlong Yang, Shanghai (CN)

(73) Assignees: FBC (SHANGHAI) PHARMACEUTICAL TECHNOLOGY CO., LTD., Shanghai (CN); KEWPIE CORPORATION, Tokyo (JP)

( * ) Notice: Subject to any disclaimer, the term of this patent is extended or adjusted under 35 U.S.C. 154(b) by 868 days.

(21) Appl. No.: 17/604,347

(22) PCT Filed: Apr. 2, 2020

(86) PCT No.: PCT/CN2020/082905
§ 371 (c)(1),
(2) Date: Oct. 15, 2021

(87) PCT Pub. No.: WO2020/211653
PCT Pub. Date: Oct. 22, 2020

(65) Prior Publication Data
US 2022/0192980 A1 Jun. 23, 2022

(30) Foreign Application Priority Data
Apr. 17, 2019 (CN) .......................... 201910308271.6

(51) Int. Cl.
*A61K 9/1272* (2025.01)
*A61K 31/047* (2006.01)
(Continued)

(52) U.S. Cl.
CPC .......... *A61K 9/1272* (2013.01); *A61K 31/047* (2013.01); *A61K 31/355* (2013.01);
(Continued)

(58) Field of Classification Search
CPC .. A61K 9/1272; A61K 31/047; A61K 31/355; A61K 31/496; A61K 31/573;
(Continued)

(56) References Cited

U.S. PATENT DOCUMENTS 8,410,076 B2 4/2013 Asaoka et al.
2007/0172520 A1 7/2007 VanAuker et al.
(Continued)

FOREIGN PATENT DOCUMENTS

CN 101316864 12/2008
CN 101715457 5/2010
(Continued)

OTHER PUBLICATIONS

And Zeng et al. (Hyaluronic acid-coated niosomes facilitate tacrolimus ocular delivery, Colloids and Surfaces B: Biointerfaces, 2016). (Year: 2016).*
(Continued)

*Primary Examiner* — Robert A Wax
*Assistant Examiner* — John Seungjai Kwon
(74) *Attorney, Agent, or Firm* — Wenderoth, Lind & Ponack, L.L.P.

(57) ABSTRACT

A cationic hyaluronic acid coated spanlastic, comprising a drug-loaded vesicle. The surface of the drug-loaded vesicle is modified by cationic hyaluronic acid, the drug-loaded vesicle comprises a vesicle membrane and a hydrophobic drug wrapped by the vesicle membrane, and the vesicle membrane comprises a nonionic surfactant and an edge activator.

9 Claims, 4 Drawing Sheets

(51) Int. Cl.

| | |
|---|---|
| *A61K 31/355* | (2006.01) |
| *A61K 31/496* | (2006.01) |
| *A61K 31/573* | (2006.01) |
| *A61K 38/13* | (2006.01) |
| *A61K 47/36* | (2006.01) |
| *A61P 27/02* | (2006.01) |

(52) U.S. Cl.
CPC .......... *A61K 31/496* (2013.01); *A61K 31/573* (2013.01); *A61K 38/13* (2013.01); *A61K 47/36* (2013.01); *A61P 27/02* (2018.01)

(58) Field of Classification Search
CPC ...... A61K 38/13; A61K 47/36; A61K 9/0048; A61K 9/5146; A61K 9/5161; A61K 31/07; A61K 47/6907; A61K 9/1273; A61P 27/02
See application file for complete search history.

(56) References Cited

U.S. PATENT DOCUMENTS

| | | |
|---|---|---|
| 2009/0281056 A1 | 11/2009 | Mori et al. |
| 2015/0098986 A1 | 4/2015 | Hsu et al. |

FOREIGN PATENT DOCUMENTS

| | | | |
|---|---|---|---|
| CN | 110063938 | | 7/2019 |
| CN | 108451908 | | 8/2021 |
| JP | 2016-108285 | | 6/2016 |
| JP | 2016108285 A | * | 6/2016 |
| KR | 10-2010-0043748 | | 4/2010 |

OTHER PUBLICATIONS

Zeng et al. (Hyaluronic acid-coated niosomes facilitate tacrolimus ocular delivery, Colloids and Surfaces B: Biointerfaces, 2016). (Year: 2016).*
Garrigue et al. (Relevance of Lipid-Based Products in the Management of Dry Eye Disease, Journal of Ocular Pharmacology and Therapeutics, 2017) (Year: 2017).*
Kakkar et al. (Spanlastics—A novel nanovesicular carrier system for ocular delivery, Pharmaceutical Nanotechnology, 2011 (Year: 2011).*
JP-2016108285-A Translated (Year: 2016).*
International Search Report dated Jun. 30, 2020 in International (PCT) Application No. PCT/CN2020/082905, with English language translation.
Liu, Y., et al., "Cationized hyaluronic acid coated spanlastics for cyclosporine A ocular delivery: Prolonged ocular retention, enhanced corneal permeation and improved tear production", International Journal of Pharmaceutics, vol. 565, pp. 133-142, May 8, 2019.
Kakkar, S., et al., "Spanlastics—A novel nanovesicular carrier system for ocular delivery", International Journal of Pharmaceutics, vol. 413, pp. 202-210, Apr. 21, 2011.
Fang, L., Non-Official Translation: "Preparation for ocular drug delivery via mucous membrane", Pharmaceutics, China Medical Science Press, Mar. 31, 2016, pp. 442-444.
Yanmei Qin et al., "Hyaluronic acid-modified cationic niosomes for ocular gene delivery: improving transfection efficiency in retinal pigment epithelium", Journal of Pharmacy and Pharmacology, vol. 70 (2018), pp. 1139-1151.
Extended European Search Report issued Nov. 23, 2022 in correpsonding European Patent Application No. 20791862.4.
Aliaa N. Elmeshad et al., "Enhanced corneal permeation and antimycotic activity of itraconazole against Candida albicans via a novel nanosystem vesicle", Drug Delivery, vol. 23, No., 7, 2016, pp. 2115-2123.
Irem Yenice et al., "Hyaluronic acid coated poly-8-caprolactone nanospheres deliver high concentrations of cyclosporine A into the cornea", Experimental Eye Research, vol. 87, 2008, pp. 162-167.
Mohd Abul Kalam, "Development of chitosan nanoparticles coated with hyaluronic acid for topical ocular delivery of dexamethasone", International Journal of Biological Macromolecules, vol. 89, 2016, pp. 127-136.
International Preliminary Report of Patentability (Chapter I) (Form PCT/IB/337) issued Sep. 28, 2021 in corresponding International Application No. PCT/CN2020/082905, 6 pages.
English translation of Fang, L., "Preparation for ocular drug delivery via mucous membrane", Pharmaceutics, China Medical Science Press, Mar. 31, 2016, pp. 442-444.

* cited by examiner (a)

(b)

CATIONIC HYALURONIC ACID COATED SPANLASTICS AND PREPARATION AND APPLICATION THEREOF

CROSS-REFERENCE TO RELATED APPLICATIONS

This application is a national stage application filed under 35 U.S.C. § 371 of international application no. PCT/CN2020/082905 filed Apr. 2, 2020, which claims priority to Chinese Patent Application No. 201910308271.6 filed Apr. 17, 2019, which is incorporated by reference in its entirety.

TECHNICAL FIELD

The present disclosure belongs to the technical field of pharmaceutical preparations, and specifically relates to a cationic hyaluronic acid coated spanlastics, a preparation method and an application thereof.

BACKGROUND

Eye is an organ capable of perceiving light and providing vision, a portal for transmitting information, and a source where we acquire most of the information. Approximately 80% of the memory and knowledge in the brain are acquired via eyes. Currently, ocular diseases caused by various reasons are on the rise, and there are up to more than 200 million population suffering from ocular diseases around the world each year. Topical ocular administration is one of the main ways to treat ocular diseases. However, the transmembrane transport of the drug is restricted due to the corneal barrier, drainage via nasolacrimal duct and the physical and chemical properties of the drug itself.

Cyclosporin, lutein, ketoconazole, α-tocopherol and dexamethasone palmitate are lipophilic macromolecular drugs. Lipophilicity may contribute to the permeation into the biological membrane, but the large molecular weight prevents them from passing through the biological membrane. In addition, it can be noted that high liposolubility is capable of ensuring the passage through the corneal epithelium while the further passage through the highly hydrophilic corneal stroma is hindered. Therefore, a drug delivery strategy must be developed to improve bioavailability to the largest extent. In addition, various physiological mechanisms exposed to the eyes after administration to the ocular surface, such as blink reflex, renewal of tear film and tear circulation, may cause partial loss of the dose. Therefore, large molecular weight, poor water solubility and limited retention time on ocular surface are the main reasons for the low bioavailability of these drugs, generally less than 5%. In addition, safety and tolerability are important considerations for products used for ophthalmic applications.

Vesicular drug delivery systems for ophthalmic preparations include liposomes and niosomes, which are capable of encapsulating a hydrophilic drug in an aqueous core and encapsulating a hydrophobic drug in a double-layer membrane so as to protect the drug from the influence of the biological environment and control the release time of the drug. A vesicle system is also capable of prolonging the duration of action on the surface of the cornea by preventing the ocular metabolism of enzymes in tear. Niosomes have advantages similar to liposomes, such as biocompatibility and biodegradability. In addition, the use of nonionic surfactants instead of phospholipids enables lower production costs and chemical stability as compared to liposomes. A spanlastic has an edge activator (such as Tween 80) added in niosome, which is capable of increasing the elasticity of the vesicle and enabling the vesicle to squeeze smaller pores by the pressure caused by the concentration gradient, thereby increasing corneal permeability.

The method of prolonging the retention time of drugs on ocular surface also includes using mucoadhesive polymers (such as chitosan, carboxymethyl cellulose, chondroitin sulfate and hyaluronic acid) as the carriers of eye drops. Hyaluronic acid (HA) is a natural component of human vitreous humor and has been widely used for ophthalmic drug delivery. Recently, many products based on HA or its derivatives have been used for treating xerophthalmia. Cationic hyaluronic acid (CHA) containing quaternary ammonium group(s) has been used in healing agents, skin modifiers and hair cosmetics and has exhibited moisturizing property better than anionic hyaluronic acid due to its adsorptive property. This feature provides with the potential for ophthalmic application.

SUMMARY

In order to overcome the shortcomings of the prior art, the object of the present disclosure is to develop a cationic hyaluronic acid coated spanlastics for drug delivery on ocular surface.

In order to achieve the above object, the present disclosure provides a cationic hyaluronic acid coated spanlastic, wherein the cationic hyaluronic acid coated spanlastic comprises a drug-loaded vesicle, the surface of the drug-loaded vesicle is modified with cationic hyaluronic acid, the drug-loaded vesicle comprises a vesicle membrane and a hydrophobic drug wrapped by the vesicle membrane, and the vesicle membrane comprises a nonionic surfactant and an edge activator.

Preferably, the hydrophobic drug is at least one of cyclosporin, lutein, ketoconazole, α-tocopherol and dexamethasone palmitate.

Preferably, the nonionic surfactant includes but is not limited to Span 40, Span 60, Span 80, Poloxamer 121 or Poloxamer 123.

Preferably, the edge activator includes but is not limited to Tween 20, Tween 40, Tween 80, sodium cholate, polyoxyethylene lauryl ether 35 or polyoxyethylene castor oil EL.

Preferably, the cationic hyaluronic acid coated spanlastic has a particle size of 200 to 310 nm, a zeta potential of −10 mV to −30 mV and a viscosity of 1 mPa·s to 12 mPa·s.

Preferably, the weight ratio of the nonionic surfactant and the edge activator is between 60:40 and 90:10.

Preferably, the weight ratio of the nonionic surfactant and the hydrophobic drug is between 20:1 and 4:1.

The methods for preparing the above-mentioned cationic hyaluronic acid coated spanlastics include but are not limited to thin-film hydration method, reverse phase evaporation method and organic solvent volatilization method.

The present disclosure also provides a method for preparing the above-mentioned cationic hyaluronic acid coated spanlastic, comprising: injecting an ethanol solution containing a nonionic surfactant and a hydrophobic drug into an aqueous solution containing an edge activator and glycerin at 65° C. to 75° C., stirring to volatilize ethanol, obtaining a dispersion of drug-loaded vesicle, adding the dispersion of drug-loaded vesicle dropwise into an isotonic solution of cationic hyaluronic acid, stirring, and obtaining a dispersion of cationic hyaluronic acid coated spanlastic.

Preferably, the isotonic solution is physiological saline solution or 2.5% glycerin aqueous solution.

Preferably, the cationic hyaluronic acid used in modification has a concentration of 0.05% w/v to 0.15% w/v (i.e., 100 mL of the dispersion of cationic hyaluronic acid coated spanlastic contains 0.05 g to 0.15 g of cationic hyaluronic acid).

The present disclosure also provides the use of the above-mentioned cationic hyaluronic acid coated spanlastic in preparation of a drug for treating ocular diseases.

In the present disclosure, the connections between cationic hyaluronic acid and the drug-loaded vesicle include but are not limited to electrostatic adhesion and hydrogen bonding.

As compared with the prior art, the present disclosure has beneficial effects as follows.

(1) A spanlastic is prepared and obtained in the present disclosure. The nonionic surfactant in the spanlastic has good stability, is not easy to oxidize, and has little eye irritation. An edge activator is used, which is capable of increasing the elasticity of the vesicle and enabling the vesicle to squeeze smaller pores by the pressure caused by the concentration gradient, thereby increasing corneal permeability.

(2) In the present disclosure, cationic hyaluronic acid is used for modifying the carrier, which prolongs the duration of action of the carrier on ocular surface and also enhances the corneal permeability of the carrier.

(3) In the present disclosure, distinguished from commercially available emulsions, castor oil, preservatives and cationic surfactants are not used. The spanlastics are in the form of colloidal solution. Dropwise administration on ocular surface will not cause irritation, has good compliance among patients, and is suitable for long-term use.

(4) The spanlastic of the present disclosure has the characteristics of prolonged duration of action on ocular surface, increased corneal permeation and corneal residual, no irritation on ocular surface and enhanced bioavailability, and is an ophthalmic drug delivery system with potential.

(5) The experiments in the present disclosure indicates that, the spanlastics shows good encapsulation effect of cyclosporin, has good corneal permeability and corneal residual as compared with the commercially available emulsions, and shows no irritation in both acute and long-term stimulation experiments. In addition, in animal models suffering from xerophthalmia, the symptom of dry eye in the animals have been found to be significantly improved via Schirmer's tear secretion test, tear ferning test, and analysis of pathological section.

(6) In the present disclosure, hydrophobic drugs are encapsulated in a double-layer or multilayer membrane, so as to protect the drug from the influence of the biological environment and control the release time of the drugs; an edge activator is added into the lipoid vesicle, which is capable of increasing the elasticity of the vesicle and enabling the vesicle to squeeze smaller pores by the pressure caused by the concentration gradient, thereby increasing corneal permeability; and cationic hyaluronic acid enhances the mucosal adhesiveness of the carrier, further enhances corneal permeability, and has certain corneal wetting effect.

DETAILED DESCRIPTION

Figure 1:
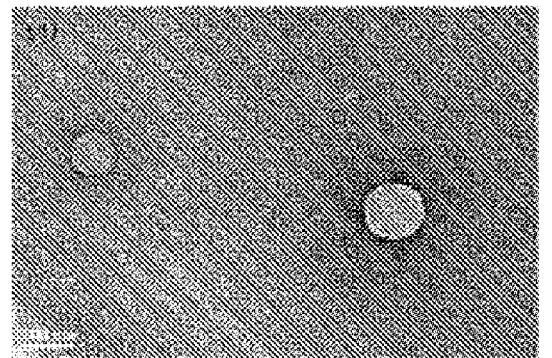
FIG. 1: Transmission electron micrographs of cyclosporin-loaded coated spanlastics (CHASVs) and cationic hyaluronic acid coated spanlastics (SVs).
Figure 1:
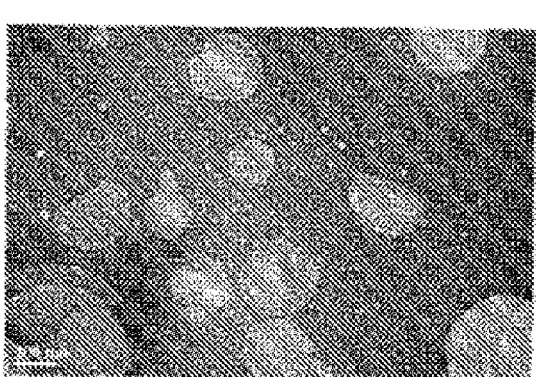

The present disclosure will be further described as below with reference to specific examples. It should be understood that these examples are merely used to illustrate the present disclosure and not to limit the scope of the present disclosure. In addition, it should be understood that those skilled in the art are capable of making various changes or modifications to the present disclosure after reading the teachings of the present disclosure, and these equivalents also fall within the scope defined by the appended claims of the present disclosure.

The raw materials used in the following examples are all commercially available products. Cationic hyaluronic acid used in the following examples is Hyaloveil™-P from Kewpie, Japan.

Examples 1 to 3

Method for Preparing Spanlastics with Deformability 0.4 g of nonionic surfactant Span 60 and 0.075 g of hydrophobic drug (cyclosporin) were accurately weighed and dissolved in 12.5 mL of absolute ethanol. The mixture was subjected to ultrasonic treatment for 1 min in a water bath and heated to 70° C. to enable complete dissolution, thereby obtaining an ethanol solution containing the nonionic surfactant and the hydrophobic drug.

Water phase: The edge activator Tween 20 (see Table 1 for the ratio of Span 60 and Tween 20) and 2.5% glycerin were dissolved in 100 mL of water, thereby obtaining an aqueous solution in which the edge activator and glycerin were dissolved.

100 mL of the aqueous solution with the edge activator dissolved therein was measured and stirred at a constant temperature of 70° C., and the rotation speed was adjusted to 800 rpm/min.

The ethanol solution containing the nonionic surfactant and the hydrophobic drug (completely dissolved) was pipetted with a syringe. The needle was placed below the liquid level of the aqueous solution with the edge activator and glycerin dissolved therein, the ethanol solution was completely injected into the aqueous solution with the edge activator and glycerin dissolved therein at a constant speed of 1 ml/min, and the resultant was further stirred for about half an hour to volatilize ethanol. An ultrafiltration cup was used, a membrane with a molecular weight cut-off of 100 kDa was adopted, and the formed vesicles were subjected to an equal volume ultrafiltration 10 times so as to remove ethanol and free drugs. An isotonic aqueous solution (2.5% aqueous glycerin solution) was added to the resulting cationic hyaluronic acid coated spanlastics until the total volume reached 100 mL, and the resultant was subjected to ultrasonic treatment for 3 min in a water bath at room temperature so as to disperse the vesicles and obtain a dispersion.

Particle size, zeta potential and PDI were measured by a particle size analyzer. The content and encapsulation efficiency of the drug were measured by high performance liquid chromatography (chromatographic conditions: octadecylsilane bonded silica was used as filler (the chromatographic column is Diamonsil Plus C18, 150 mm×4.6 mm, 5 μm); acetonitrile-methanol-water (62:5:33) was used as the mobile phase; methanol was used as the diluent; the detection wavelength was 210 nm; and the column temperature was 70° C.). The spanlastics were extruded through a polycarbonate membrane filter with a pore size of 100 nm, and the particle sizes before and after extrusion were measured. The elasticity of the spanlastics was evaluated based on the deformation index. The deformation index was calculated as follows: $D=j/t\ (r_v/r_p)^2$. Among them, D denoted deformation index (ml/s), j denoted extrusion volume (ml), t denoted extrusion period (s), $r_v$ denoted the vesicle size after extrusion (nm), and $r_p$ denoted the pore size of the filter membrane (nm).

Span 60 and Tween 20 were respectively used as the nonionic surfactant and the edge activator for the experiments.

TABLE 1

| Sample name | Span 60: Tween 20 (w/w) | Size (nm) | PDI | Zeta potential mV | Deform-ability index ml/s | Encap-sulation efficiency (%) |
|---|---|---|---|---|---|---|
| Example 1 | 9:1 | 293.5 | 0.222 | −18.0 | 6.37 | 94.7 |
| Example 2 | 8:2 | 269.0 | 0.215 | −17.1 | 8.58 | 94.9 |
| Example 3 | 7:3 | 232.1 | 0.222 | −17.3 | 7.33 | 89.2 |

The addition of the edge activator increased the fluidity of the membrane, the spanlastics were capable of squeezing themselves to pass through the intercellular region via the influence of the water gradient based on the bending energy of the membrane, and it could be seen from the above table that Example 2 exhibited the highest deformation index. The drug content of Example 3 was relatively low, which was probably due to the fact that the edge activator improved the fluidity of the two lipid layers and thus resulted in the leakage of the drug within the bimolecular layers.

Examples 4 to 28

Preparation of Spanlastics with Deformability

The preparation was similar to that of Example 2, except that different nonionic surfactants and edge activators were used to prepare spanlastics.

TABLE 2

| Sample name | surfactant | edge activator | Size (nm) | PDI | Zeta potential (mV) | Deform-ability index (ml/s) |
|---|---|---|---|---|---|---|
| Example 4 | Span 40 | Tween 20 | 186.8 | 0.216 | −15.8 | 3.83 |
| Example 5 | Span 40 | Tween 80 | 198.6 | 0.238 | −17.0 | 3.89 |
| Example 6 | Span 40 | sodium cholate | 269.0 | 0.269 | −20.2 | 4.12 |
| Example 7 | Span 40 | polyoxyethylene lauryl ether 35 | 154.7 | 0.356 | −19.3 | 3.27 |
| Example 8 | Span 40 | polyoxyethylene castor oil EL | 202.9 | 0.160 | −20.6 | 6.77 |
| Example 9 | Span 60 | Tween 20 | 287.2 | 0.178 | −17.4 | 6.55 |
| Example 10 | Span 60 | Tween 80 | 269.0 | 0.215 | −17.8 | 8.58 |
| Example 11 | Span 60 | sodium cholate | 401.3 | 0.355 | −20.8 | 9.02 |
| Example 12 | Span 60 | polyoxyethylene lauryl ether 35 | 254.8 | 0.432 | −19.7 | 5.47 |

TABLE 2-continued

| Sample name | surfactant | edge activator | Size (nm) | PDI | Zeta potential (mV) | Deform-ability index (ml/s) |
|---|---|---|---|---|---|---|
| Example 13 | Span 60 | polyoxyethylene castor oil EL | 314.6 | 0.391 | −21.8 | 8.21 |
| Example 14 | Span 80 | Tween 20 | 298.0 | 0.302 | −18.6 | 6.32 |
| Example 15 | Span 80 | Tween 80 | 302.6 | 0.298 | −17.6 | 8.29 |
| Example 16 | Span 80 | sodium cholate | 512.6 | 0.404 | −21.7 | 8.55 |
| Example 17 | Span 80 | polyoxyethylene lauryl ether 35 | 306.5 | 0.396 | −19.4 | 7.07 |
| Example 18 | Span 80 | polyoxyethylene castor oil EL | 374.64 | 0.162 | −23.9 | 8.00 |
| Example 19 | Poloxamer 121 | Tween 20 | 256.7 | 0.346 | −13.9 | 7.21 |
| Example 20 | Poloxamer 121 | Tween 80 | 245.8 | 0.412 | −15.4 | 6.76 |
| Example 21 | Poloxamer 121 | sodium cholate | 303.5 | 0.356 | −19.7 | 10.84 |
| Example 22 | Poloxamer 121 | polyoxyethylene lauryl ether 35 | 287.7 | 0.645 | −18.6 | 9.05 |
| Example 23 | Poloxamer 121 | polyoxyethylene castor oil EL | 278.3 | 0.465 | −20.0 | 9.45 |
| Example 24 | Poloxamer 123 | Tween 20 | 266.6 | 0.298 | −15.5 | 6.09 |
| Example 25 | Poloxamer 123 | Tween 80 | 276.7 | 0.404 | −18.4 | 7.57 |
| Example 26 | Poloxamer 123 | sodium cholate | 378.1 | 0.376 | −20.6 | 7.89 |
| Example 27 | Poloxamer 123 | polyoxyethylene lauryl ether 35 | 284.0 | 0.534 | −19.2 | 8.56 |
| Example 28 | Poloxamer 123 | polyoxyethylene castor oil EL | 246.2 | 0.468 | −22.0 | 10.02 |

Examples 29 to 32

Preparation Method of Drug-Loaded Spanlastics

The preparation was similar to that of Example 10, except that the hydrophobic drug (cyclosporin)-loaded spanlastics were prepared at different drug-to-lipid ratios. The appropriate drug-to-lipid ratio was selected via encapsulation efficiency and storage stability (the spanlastics were left at 4° C. for two weeks, leakage rate=(encapsulation efficiency measured two weeks ago−encapsulation efficiency measured two weeks later)).

TABLE 3

| Sample name | drug-lipid ratio (w:w) | Size (nm) | PDI | Zeta potential mV | Encap-sulation efficiency (w/w) % | Leakage rate after being left for two weeks (w/w) % |
|---|---|---|---|---|---|---|
| Example 29 | 1:20 | 227.1 | 0.193 | −17.4 | 92.7 | 0.7% |
| Example 30 | 1:10 | 269.0 | 0.215 | −16.6 | 94.9 | 1.2% |
| Example 31 | 1:5 | 291.9 | 0.180 | −17.0 | 95.2 | 2.4% |
| Example 32 | 1:4 | 302.0 | 0.165 | −17.3 | 94.2 | 9.4% |

Examples were compared. With the increase of the amount of the encapsulated drug, the particle size of the spanlastic increased, and the drug leakage within two weeks increased. As shown in FIG. 1(a), Example 31 had relatively high drug loading capacity and was more stable as compared with other Examples, and was capable of forming uniform and stable double-layer or multi-layer nanovesicles.

Examples 33 to 37

Preparation Method of Drug-Loaded Spanlastics

The formulation of the cyclosporin spanlastics of Example 31 was used, lutein, ketoconazole, α-tocopherol and dexamethasone palmitate were respectively loaded, and ultrafiltration was not utilized to remove impurities. The encapsulation efficiency of the drug was measured.

TABLE 4

| Sample name | Drug | Size (nm) | PDI | Zeta potential (mV) | Encapsulation efficiency (% w/w) |
|---|---|---|---|---|---|
| Example 33 | ciclosporin | 227.1 | 0.193 | −17.1 | 76.3 |
| Example 34 | lutein | 169.0 | 0.127 | −20.6 | 73.7 |
| Example 35 | ketoconazole | 154.8 | 0.167 | −15.4 | 68.8 |
| Example 36 | α-tocopherol | 152.6 | 0.069 | −20.0 | 80.0 |
| Example 37 | dexamethasone palmitate | 248.9 | 0.179 | −18.2 | 56.4 |

Examples 38 to 42

A cationic hyaluronic acid coated cyclosporin spanlastic comprises a drug-loaded vesicle, the surface of the drug-loaded vesicle is modified with cationic hyaluronic acid, the drug-loaded vesicle comprises a vesicle membrane and cyclosporin wrapped by the vesicle membrane, and the vesicle membrane contains a nonionic surfactant and an edge activator.

A dispersion of cyclosporin-loaded spanlastic was prepared according to the method of Example 33. The dispersion was added dropwise into an isotonic solution of 2% cationic hyaluronic acid (CHA) (2.5% aqueous glycerin solution). The mixture was subjected to magnetic stirring at ambient temperature for 1 hour, so as to obtain the dispersion of cationic hyaluronic acid coated spanlastics (CHASVs). The particle size, pH, zeta potential, surface tension and contact angle of each carrier were measured, and the viscosity was measured by using a rheometer at ambient temperature. The shear rate was gradually increased from 0 $s^{-1}$ to 300 $s^{-1}$.

TABLE 5

| Sample name | Amount of CHA used for modification (% w/v) | Particle size (nm) | PDI | Zeta potential (mV) | Viscosity (mPa · s) | Surface tension (mN/m) | Contact angle |
|---|---|---|---|---|---|---|---|
| Example 38 | 0 | 261.8 | 0.161 | −15.6 | 1.98 | 34.75 | 43.07 |
| Example 39 | 0.05 | 292.1 | 0.195 | −21.6 | 2.06 | 34.76 | 30.01 |
| Example 40 | 0.075 | 286.1 | 0.236 | −22.1 | 5.89 | 34.77 | 24.63 |
| Example 41 | 0.1 | 296.5 | 0.231 | −24.4 | 7.88 | 34.82 | 22.56 |
| Example 42 | 0.15 | 308.9 | 0.264 | −25.2 | 9.48 | 34.98 | 21.01 |

Each carrier was observed under a JEM-2100 mode transmission electron microscope. As could be seen from FIG. 1(a), in a case where no cholesterol was added, nonionic surfactants Span 60 and Tween 80 were capable of self-assembling and forming double-layer or multi-layer vesicles. As could be seen from FIG. 1(b), cationic hyaluronic acid formed a single-layer coating shell with irregular shape around SVs. Cationic hyaluronic acid probably bound to the surface of spanlastics via weak electrostatic adhesion and hydrogen bonding. Increasing the amount of CHA used for modification resulted in the increase of the particle size and PDI of the carrier. However, hyaluronic acid was contained in the inherent formulation of vitreous body and could be used as thickener. Although increasing the amount of hyaluronic acid could not contribute to further modification, hyaluronic acid could be dispersed in the colloidal solution of spanlastics to increase the viscosity of the preparation.

Application Examples

The resulting dispersion of Example 38 (SVs), Example 40 (0.075% w/v CHA-modified SVs) and Example 42 (0.15% w/v CHA-modified SVs) of the present disclosure were used as samples to evaluate and investigate in-vitro corneal permeation and corneal residual, ocular drug tolerance and in-vivo pharmacodynamics.

1. Corneal Permeation and Corneal Residual of Cationic Hyaluronic Acid Coated Spanlastics 1.1 Corneal permeation: A rabbit was sacrificed by intravenous injection of air via the marginal ear vein, the eyeballs were taken out, and the cornea was separated. The fresh isolated cornea was carefully fixed between the supplying tank and the receiving tank of the diffusion tank, and the epithelial layer of the cornea faced the supplying tank. Glutathione-sodium bicarbonate Ringer's solution (GBR) was formulated as a diffusion medium. GBR solution was composed of two solutions, one solution contained 12.4 g/L sodium chloride, 0.716 g/L potassium chloride, 0.233 g/L sodium dihydrogen phosphate dehydrate and 4.908 g/L sodium bicarbonate, and the other solution contains 0.174 g/L anhydrous calcium chloride, 0.349 g/L magnesium chloride hexahydrate, 1.8 g/L glucose and 0.184 g/L oxidized glutathione. The two solutions mentioned above were stored at low temperature and mixed in equal volume immediately before use. 7 ml of GBR solution (glutathione-sodium bicarbonate Ringer's solution) containing 2% SDS at 37° C. was added into the supplying tank and the receiving tank, respectively. After the system was equilibrated for 10 min, the solution in the supplying tank was removed and replaced with a sample solution in the experimental group. The water bath was controlled to circulate at 37° C., and a mixed gas of $O_2$ and $CO_2$ (95%:5%) was slowly bubbled into the GBR solution. At 30 min, 60 min, 90 min, 120 min, 150 min, 180 min, 240 min and 300 min after the start of the experiment, 200 μl of sample was taken from the receiving cell, and an equal volume of GBR solution preheated at 37° C. was supplemented immediately so as to maintain a constant volume of the solution in the diffusion tank. 20 μl of the sample was taken and measured by HPLC. The concentration (μg/ml) of the sample at each sampling point was calculated, and cumulative penetration amount Qn (μg) and apparent permeability coefficient $P_{app}$ (cm/s) were calculated by the following formula.

$$Q_n = V_0 \left( C_n + \frac{V}{V_0} \sum_{i=1}^{n-1} C_i \right) = V_0 C_n + V \sum_{i=1}^{n-1} C_i, \quad P_{app} = \frac{\Delta Q_n}{\Delta t} \cdot \frac{1}{C_0 \cdot A \cdot 60},$$

Among them, Co was the initial drug concentration in the supplying tank (μg·cm$^{-3}$), A was the effective permeable area (cm$^2$), $\Delta Q_n/\Delta t$ could be determined by the slope of the steady state of the cumulative penetration amount-time curve (μg·min$^{-1}$), $C_i$ was the concentration measured at the i-th sampling, n was the number of sampling, $V_0$ was the liquid volume of the receiving tank, V was the sampling volume, and $C_n$ was the concentration of the sample obtained from the n-th sampling.

1.2 Corneal hydration extent: After the experiment, corneal hydration value H was calculated as follows:

$$H: H\% = \frac{m_b - m_a}{m_b} \times 100\%.$$

Among them, $m_b$ was the wet weight of the permeable part of the cornea at the end of the permeation experiment, that is, after the permeation experiment, the scleral ring used for fixing at corneal edge was incised, and the cornea was weighed and the weight was recorded as $m_b$. Afterwards, this cornea was dried at 40° C. to a constant weight, which was recorded as $m_a$.

1.3 Corneal residue: After the completion of the ex-vivo corneal permeation experiment, the cornea used therein was removed and rinsed, dried in the air and then weighed accurately. The resultant was placed into a glass homogenization tube and 1 ml of methanol was added. The mixture was homogenized and centrifuged, the supernatant was taken and measured by HPLC, and the chromatographic conditions were the same as those for content determination. Preparation of the standard curve of the drug in cornea: Methanol solutions (1 ml) of different concentrations of cyclosporine were added to blank cornea, the mixture was homogenized and centrifuged, and the supernatant was taken and measured by HPLC.

TABLE 6

| | $P_{app}(\times 10^{-6}$ cm/s) | CsA corneal residue (μg/g) |
|---|---|---|
| SVs | 4.05 ± 0.87 | 153.30 ± 1.02 |
| 0.075% w/v CHASVs | 4.49 ± 1.11 | 246.83 ± 2.17 |
| 0.15% w/v CHASVs | 5.22 ± 1.20 | 312.18 ± 1.34 |

Figure 2:
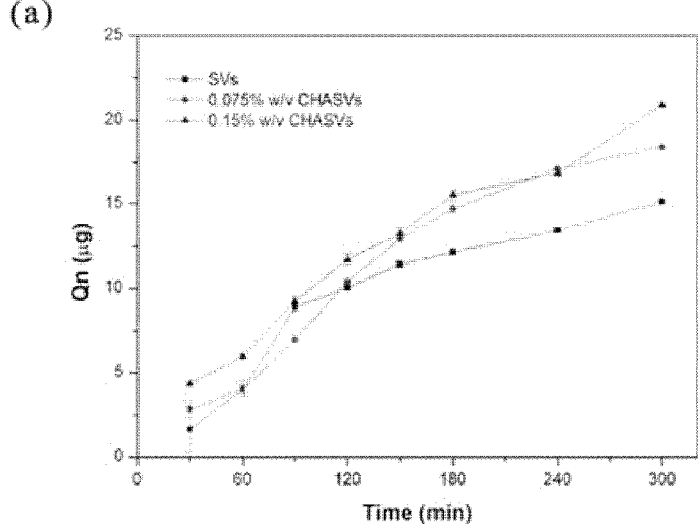
FIG. 2: Experimental results of corneal permeation (a) and corneal hydration (b).
Figure 2:
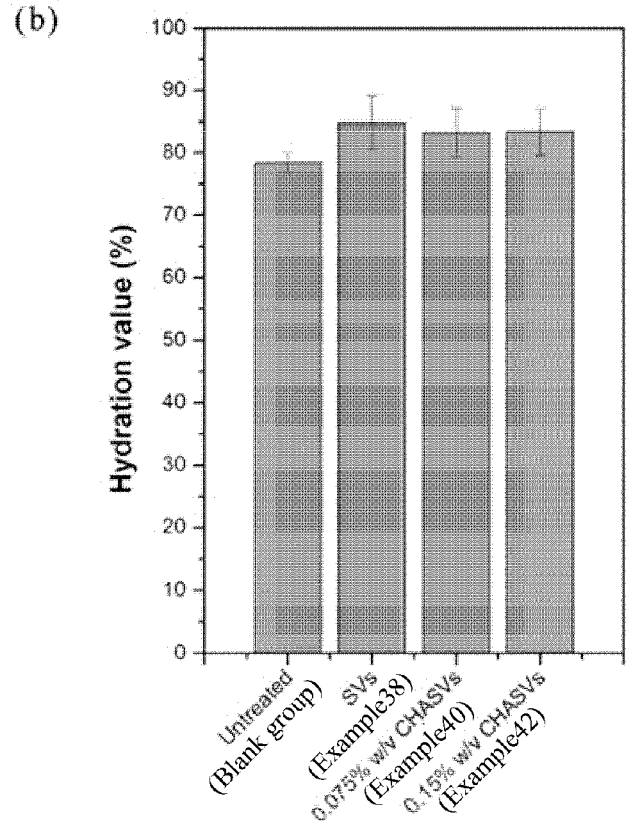

The experimental results were as shown in Table 4 and FIG. 2. The spanlastics (SVs) had increased vesicle elasticity due to the addition of the edge activator, and the corneal permeation was greater than that of niosomes. The corneal permeation was significantly increased after the modification by cationic hyaluronic acid, and the higher the amount used for modification, the higher the permeability, indicating that CHA was capable of significantly enhancing the corneal permeation of drugs. CsA residue in the cornea of the SVs experimental group was relatively large, which was probably due to the mechanism of vesicle infiltration, i.e., the drug that was first absorbed by the corneal surface and then wrapped was transported to the epithelial cell membrane of the cornea and then passively diffused and transported. As compared with SVs, CHA-modified vesicles caused significant increase of the residual amount of drug in the cornea, and the residual amount increased with the increase of the amount of CHA used for modification, indicating that CHA was capable of further promoting the contact fusion between the preparation and cornea and enabling the reduction of the contact angle, which was conducive to the uniformity of spreading and wetting. In addition, the measurement results of ex-vivo corneal hydration values in corneas incubated with each preparation showed no significant difference when compared with the blank group (P>0.05), indicating that the preparations used in the in-vitro experiments caused no damage to cornea. In summary, SVs and CHASVs were ophthalmic drug delivery systems with potential.

10

2. In-Vivo Safety Study of Cationic Hyaluronic Acid Coated Spanlastics

A rabbit was fixed on a stand for fixing rabbit, 100 μl of the sample was dripped into the conjunctival sacs in both eyes, and the eyelids were closed to allow the drug to distribute evenly. Acute irritation: The eyes of the rabbit were administered with 3 consecutive doses with an interval of 5 min, and the indicators for eyes were each examined 30 min after the last administration. Long-term irritation: The eyes of the rabbit were administered 5 times daily for 7 consecutive days. 2 h after the last administration, the indicators for eyes were each examined according to the scoring criteria for Draize eye irritation test.

Figure 3:
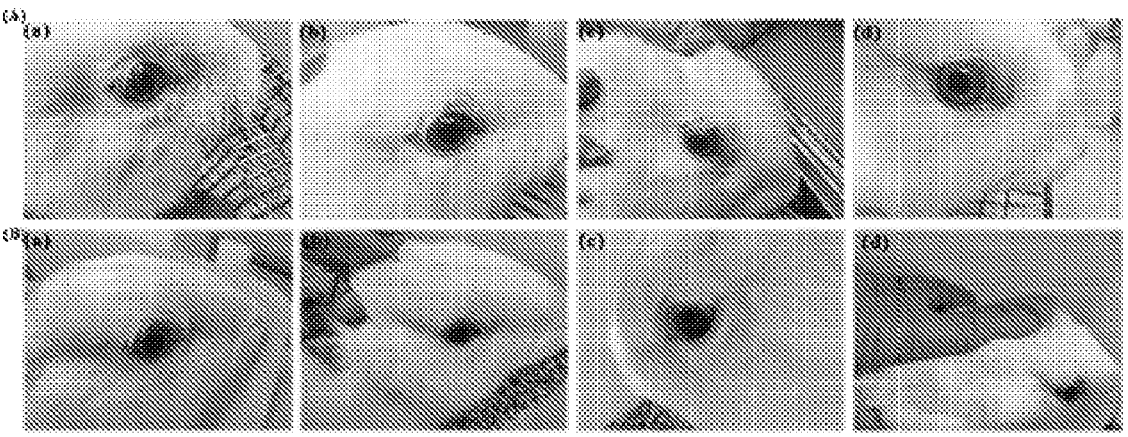
FIG. 3: Experimental results of acute (A) and long-term (B) irritation.

The experimental results were as shown in FIG. 3, wherein (a) denoted the non-administered group, (b) denoted SVs group, (c) denoted 0.075% w/v CHASVs group, and (d) denoted 0.15% w/v CHASVs group. In the acute stimulation experiment, the non-administered group was used as control, both SVs group and CHASVs group did not show signs of inflammation, edema and the like. In the long-term experiment, the scores of Draize eye irritation in all groups were also 0, indicating that long-term administration of SVs and CHASVs had no irritation and was suitable for long-term ocular administration.

3. In-Vivo Pharmacodynamic Evaluation of Cationic Hyaluronic Acid Coated Spanlastics 3.1 Induction of a Xerophthalmia Animal Model In order to induce xerophthalmia, 1% atropine sulfate solution was infused into both eyes of the rabbit. At 9 am, 2 μm and 7 pm, 50 μL of atropine sulfate solution was dripped into the inferior conjunctival sacs of both eyes of the rabbit for 5 consecutive days.

3.2 Dosage Regimen

At 9 am, 2 μm and 7 pm, 50 μL of the sample solution was dripped 5 minutes after each administration of atropine sulfate solution, and the treatment continued for five days. The basic secretion of tear was determined by Schirmer tear test, fern-like crystal in tear was observed under optical microscope, and goblet cells was observed by histological analysis.

3.3 Schirmer's Tear Test

Schirmer's tear test (STT) was conducted to determine the basic secretion of tear. Topical anesthetic was dripped into the eye, after the excess tear was aspirated from the eye, a 5×35 mm graduated test paper was taken, folded at one end by 5 mm, and gently put into the outer ⅓ of the inferior conjunctival sac of the tested eye. The filter paper was taken out after 5 min, the wetted length was measured, and 10 mm to 30 mm/5 min was generally considered as normal. If the wetted length was less than 5 mm, it could be diagnosed as lack of tear; if the wetted length was 6 to 10 mm, it could be suspiciously diagnosed as reduced secretion; and if the wetted length was more than 10 mm, it could be considered as normal. If the filter paper was fully wet in less than 5 minutes, the time when the filter paper was fully wet was recorded.

Figure 4:
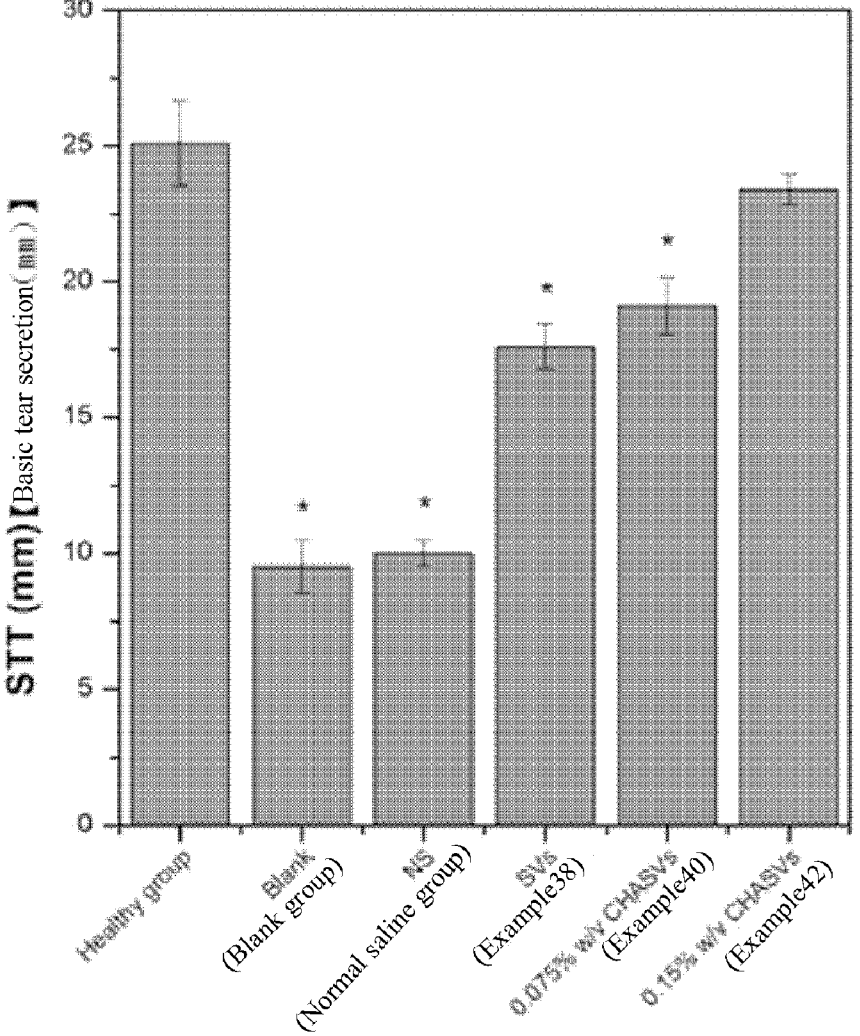
FIG. 4: Experimental results of Schirmer's tear secretion test.

The experimental results were as shown in FIG. 4. The eye of rabbit was used as the research object, and different methods were adopted to treat xerophthalmia. As compared with the healthy group, the tear secretion amount of the eyes of rabbit suddenly decreased and STT score was lower than 10 in the blank group, indicating the successful induction of xerophthalmia. The score did not increase significantly after NS treatment. After treatment with SVs and CHASVs, the tear secretion of rabbits was significantly increased, indicating the amelioration of dry eye symptom. STT results also demonstrated that the improvement of the inhibitory effect of CHASVs on xerophthalmia was related to the amount of CHA used for modification. When the concentration of the CHA used in modification was increased to 0.15% w/v, the tear secretion showed no significant difference as compared with that of the healthy group.

3.4 Tear Ferning Test

This examination was used to examine the shape of tears and the secretion function of the lacrimal gland. Tears in lacrimal lake was aspirated by using a capillary tube and dropped on a glass slide. After drying at room temperature for 10 min, the crystallization was observed under an optical microscope at a magnification of 400 times. Evaluation criteria: Fern-like crystals in tear were classified into 4 types as below according to its integrity, uniformity and branching state: Type I included Type Ia and Type Ib, Type Ia had fern-like branches that were thick, big and dense, Type Ib had relatively thin and small branches with gap; Type II had small fern-like branches, the field of view was blank, and the crystals were snowflake crystals; Type III had few crystals and no fern-like branch was formed; Type IV only showed beaded mucus. Type I was normal crystal while other types were abnormal crystals.

Figure 5:
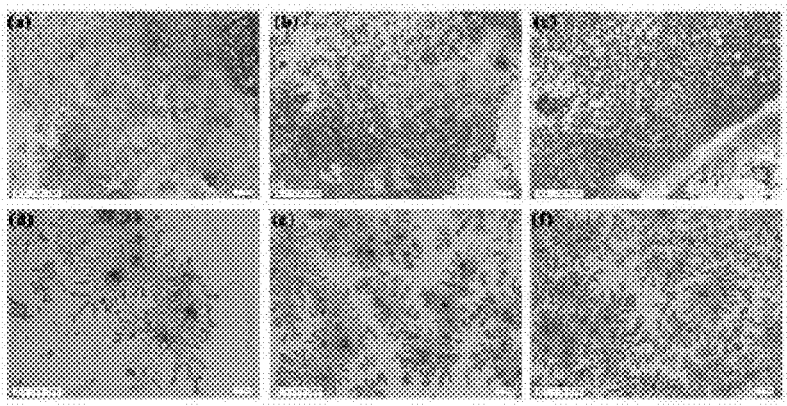
FIG. 5: Experimental results of tear ferning test.

The experimental results were as shown in FIG. 5, wherein (a) denoted the healthy group, (b) denoted xerophthalmia group, (c) denoted normal saline treatment group, (d) denoted SVs treatment group, (e) denoted 0.075% w/v CHASVs treatment group, and (f) denoted 0.15% w/v CHASVs treatment group. In atropine sulfate induction group, the fern-like crystals in tear were Type II and the fern-like branches in tear were small and formed incompletely, reflecting the successful induction of xerophthalmia. The morphology of the fern-like crystals in tear was not improved significantly in normal saline treatment group. The fern-like crystals in SVs treatment group were Type Ib with relatively thin and small branches with gap. After the treatment with CHASVs, the fern-like branches were thick, big and dense, reverting to Type Ia. The results indicated that SVs were capable of improving the secretion function of the lacrimal gland and better therapeutic effects could be achieved after CHA modification.

3.5 Histological Analysis

Rabbit was sacrificed by air embolism after administration. Eyeballs were incised, fixed with formaldehyde, embedded with paraffin, and prepared into pathological tissue sections. The sections were subjected to hematoxylin-eosin staining and examined under microscope, so as to observe whether the morphology of epidermal cells and basal cells were normal and whether there were infiltration of inflammatory cells (eosinocytes, neutrophilic granulocytes, mastocytes and lymphocytes) and morphologic changes of tissues, as well as observing the cell density of conjunctival goblet cells and epithelial morphology.

Figure 6:
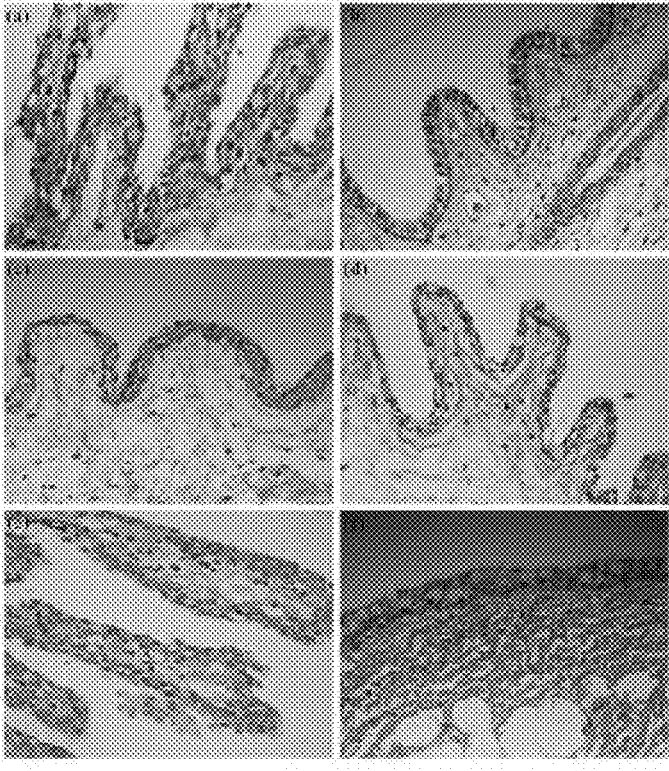
FIG. 6: Histological analysis results.

The experimental results were as shown in FIG. 6, wherein (a) denoted the healthy group, (b) denoted xerophthalmia group, (c) denoted normal saline treatment group, (d) denoted SVs treatment group, (e) denoted 0.075% w/v CHASVs treatment group, and (f) denoted 0.15% w/v CHASVs treatment group. Human conjunctival goblet cells were the main source of mucin and played an important role in maintaining normal function of ocular surface. Reduced secretion of mucin probably caused unstable tear film, resulting in poor lubrication on ocular surface. Therefore, the number of goblet cells was a key indicator reflecting the health of ocular surface. CsA was capable of increasing the cell density of goblet cells in the bulbar conjunctiva of patients suffering from xerophthalmia. It could be seen from FIG. 6 that, as compared with the healthy group, the number of conjunctival goblet cells in the atropine sulfate induction group was significantly reduced, reflecting the successful induction of xerophthalmia. As compared with the saline group, the number of conjunctival goblet cells in CsA administration groups increased, indicating the improvement of the function of ocular surface. Therefore, all preparations could be targeted to ocular surface by topical administration to inhibit xerophthalmia. After CHA modification, the number of goblet cells increased significantly, indicating that CHA was capable of improving the bioavailability of CsA. Therefore, cationic hyaluronic acid coated spanlastic was an ophthalmic drug delivery system with potential.

What is claimed is:

1. A cationic hyaluronic acid coated spanlastic, wherein the cationic hyaluronic acid coated spanlastic comprises a drug-loaded vesicle, a surface of the drug-loaded vesicle is modified with cationic hyaluronic acid, the drug-loaded vesicle comprises a vesicle membrane and a hydrophobic drug wrapped by the vesicle membrane, and the vesicle membrane comprises a nonionic surfactant and an edge activator, wherein the edge activator comprises at least one selected from the group consisting of polyoxyethylenesorbitan monolaurate (CAS RN 9005-64-5), polyoxyethylene-sorbitan monopalmitate (CAS RN 9005-66-7), polyethylene glycol sorbitan monooleate (CAS RN9005-65-6), sodium cholate, polyoxyethylene lauryl ether 35 and polyoxyethylene castor oil, and wherein the cationic hyaluronic acid coated spanlastic has a particle size of 200 nm to 310 nm, a zeta potential of −10 mV to −30 mV and a viscosity of 1 mPas to 12 mPa·s.

2. The cationic hyaluronic acid coated spanlastic of claim 1, wherein the hydrophobic drug is at least one selected from the group consisting of cyclosporin, lutein, ketoconazole, α-tocopherol and dexamethasone palmitate.

3. The cationic hyaluronic acid coated spanlastic of claim 1, wherein the nonionic surfactant comprises at least one selected from the group consisting of sorbitan monopalmitate (CAS RN 26266-57-9), sorbitane monostearate (CAS RN 1338-41-6) and sorbitane monooleate (CAS RN 1338-43-8).

4. The cationic hyaluronic acid coated spanlastic of claim 1, wherein a weight ratio of the nonionic surfactant to the edge activator is between 60:40 and 90:10.

5. The cationic hyaluronic acid coated spanlastic of claim 1, wherein a weight ratio of the nonionic surfactant to hydrophobic drug is between 20:1 and 4:1.

6. A method for preparing the cationic hyaluronic acid coated spanlastic of claim 1, comprising:

injecting an ethanol solution comprising a nonionic surfactant and a hydrophobic drug into an aqueous solution comprising an edge activator and glycerin at 65° C. to 75° C., stirring to volatilize ethanol and obtaining a dispersion of drug-loaded vesicle, adding the dispersion of drug-loaded vesicle dropwise into an isotonic solution of cationic hyaluronic acid, stirring to obtain a dispersion of cationic hyaluronic acid coated spanlastic, and obtaining the cationic hyaluronic acid coated spanlastic.

7. The method for preparing the cationic hyaluronic acid coated spanlastic of claim 6, wherein the isotonic solution of cationic hyaluronic acid has a cationic hyaluronic acid concentration of 0.05% w/v to 0.15% w/v.

8. A method of treating an ocular disease, comprising administering a therapeutically effective amount of the cationic hyaluronic acid coated spanlastic of claim 1 to a subject in need thereof.

9. The cationic hyaluronic acid coated spanlastic of claim 1, wherein the hydrophobic drug is cyclosporin.

* * * * *